United States Patent
Schlösser et al.

(10) Patent No.: US 7,410,789 B2
(45) Date of Patent: Aug. 12, 2008

(54) PROCESS FOR THE FERMENTATIVE PRODUCTION OF S-ADENOSYLMETHIONINE

(75) Inventors: Thomas Schlösser, Wolfratshausen (DE); Susanne Leonhartsberger, München (DE); Renate Flinspach, Dietramszell (DE)

(73) Assignee: Wacker Chemie AG, Munich (DE)

(*) Notice: Subject to any disclaimer, the term of this patent is extended or adjusted under 35 U.S.C. 154(b) by 0 days.

(21) Appl. No.: 11/366,315

(22) Filed: Mar. 2, 2006

(65) Prior Publication Data

US 2006/0211095 A1 Sep. 21, 2006

(51) Int. Cl.
C12N 1/21 (2006.01)
C12P 21/00 (2006.01)
C12P 13/12 (2006.01)
C12N 15/00 (2006.01)
C07K 14/00 (2006.01)
C07H 21/00 (2006.01)

(52) U.S. Cl. .............. 435/252.33; 435/252.3; 435/69.1; 435/320.1; 435/440; 435/113; 530/350; 536/23.1

(58) Field of Classification Search .............. 435/252.3, 435/69.1, 440, 113, 252.33; 530/350; 536/23.1
See application file for complete search history.

(56) References Cited

U.S. PATENT DOCUMENTS 4,562,149 A 12/1985 Shiozaki et al.

FOREIGN PATENT DOCUMENTS

| DE | 33 29 218 A1 | 3/1984 |
| DE | 102 47 437 A1 | 4/2004 |
| DE | 103 09 856 A1 | 9/2004 |
| DE | 102 49 642 A1 | 5/2005 |
| EP | 0 162 323 A1 | 11/1985 |
| EP | 0 647 712 A1 | 4/1995 |
| EP | 1 091 001 A1 | 4/2001 |
| EP | 1 457 569 A1 | 9/2004 |
| JP | 2000-139471 | 5/2000 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sousa et al., Microbiology 148(Pt5):1291-1303, 2002.*
Adler et al., Biochemistry 43:518-525, 2004.*
Adler et al., The Journal of Biological Chemistry, vol. 280, No. 4, 2005, pp. 2721-2729.
Adler et al., The Journal of Biological Chemistry, vol. 279, No. 10, 2004, pp. 8957-8965.
Derwent Abstract Corresponding to EP 1 457 569 A1.
Derwent Abstract Corresponding to DE 33 29 218 A1.
Derwent Abstract Corresponding to DE 102 47 437 A1.
Derwent Abstract Corresponding to DE 102 49 642 A1.
Derwent Abstract Corresponding to DE 103 09 856 A1.
Derwent Abstract Corresponding to JP 2000—139471.
Shiozaki et al., "S-Adenosyl-L-methionine Production by Saccharomyces sake: Optimization of the Culture Conditions for the Production of Cells with a High S-Adenosyl-L-methionine Content", Agric. Biol. Chem., vol. 53, No. 12, 1989, pp. 3269-3274.
Shiozaki et al., "Production of S-adenosyl-L-methionine by Saccharomyces sake", Journal of Biotechnology, vol. 4, 1986, pp. 345-354.
Schlenk et al., "The Production of S-Adenosyl-L-Methionine and S-Adenosyl-L-Ethionine by Yeast", Enzymologia 29, 1965, pp. 283-298.
Schlenk et al., "The Formation of S-Adenosylmethionine in Yeast", J. Biol. Chem. 229, 1957, pp. 1037-1050.
Gál et al., "The metD D-Methionine Transporter Locus of *Escherichia coli* Is an ABC Transporter Gene Cluster", Journal of Bacteriology, vol. 184, No. 17, 2002, pp. 4930-4932.
Zhang et al., "A transporter of *Escherichia coli* specific for L- and D-methionine is the prototype for a new family within the ABC superfamily", Arch. Microbiol., vol. 180, 2003, pp. 88-100.
Merlin et al., "The *Escherichia coli* metD Locus Encodes an ABC Transporter Which Includes Abc (MetN), YaeE (MetI), and YaeC (MetQ)", Journal of Bacteriology, vol. 184, No. 19, 2002, pp. 5513-5517.
Bibi et al., "MdfA, an Interesting Model Protein for Studying Multidrug Transport", J. Mol. Microbiol. Biotechnol., vol. 3, No. 2, 2001, pp. 171-177.
Nilsen et al., "Isolation of cmr, a Novel *Escherichia coli* Chloramphenicol Resistance Gene Encoding a Putative Efflux Pump", Journal of Bacteriology, vol. 178, No. 11, 1996, pp. 3188-3193.
Edgar et al., "MdfA, an *Escherichia coli* Multidrug Resistance Protein with an Extraordinarily Broad Spectrum of Drug Recognition", Journal of Bacteriology, vol. 179, No. 7, 1997, pp. 2274-2280.
Edgar et al., "A single membrane-embedded negative charge is critical for recognizing positively charged drugs by the *Escherichia coli* multidrug resistance protein MdfA", The EMBO Journal, vol. 18, No. 4, 1999, pp. 822-832.
Internet Inquiry, "S-Adenosylmethionine", National Library of Medicine (Specialized Information Services), Sep. 12, 2005, 2 pages.

* cited by examiner

*Primary Examiner*—Delia M Ramirez
(74) *Attorney, Agent, or Firm*—Brooks Kushman P.C.

(57) ABSTRACT

A microorganism strain secreting S-adenosylmethionine having increased activity of the cmr (mdfA) gene product is provided.

6 Claims, 2 Drawing Sheets

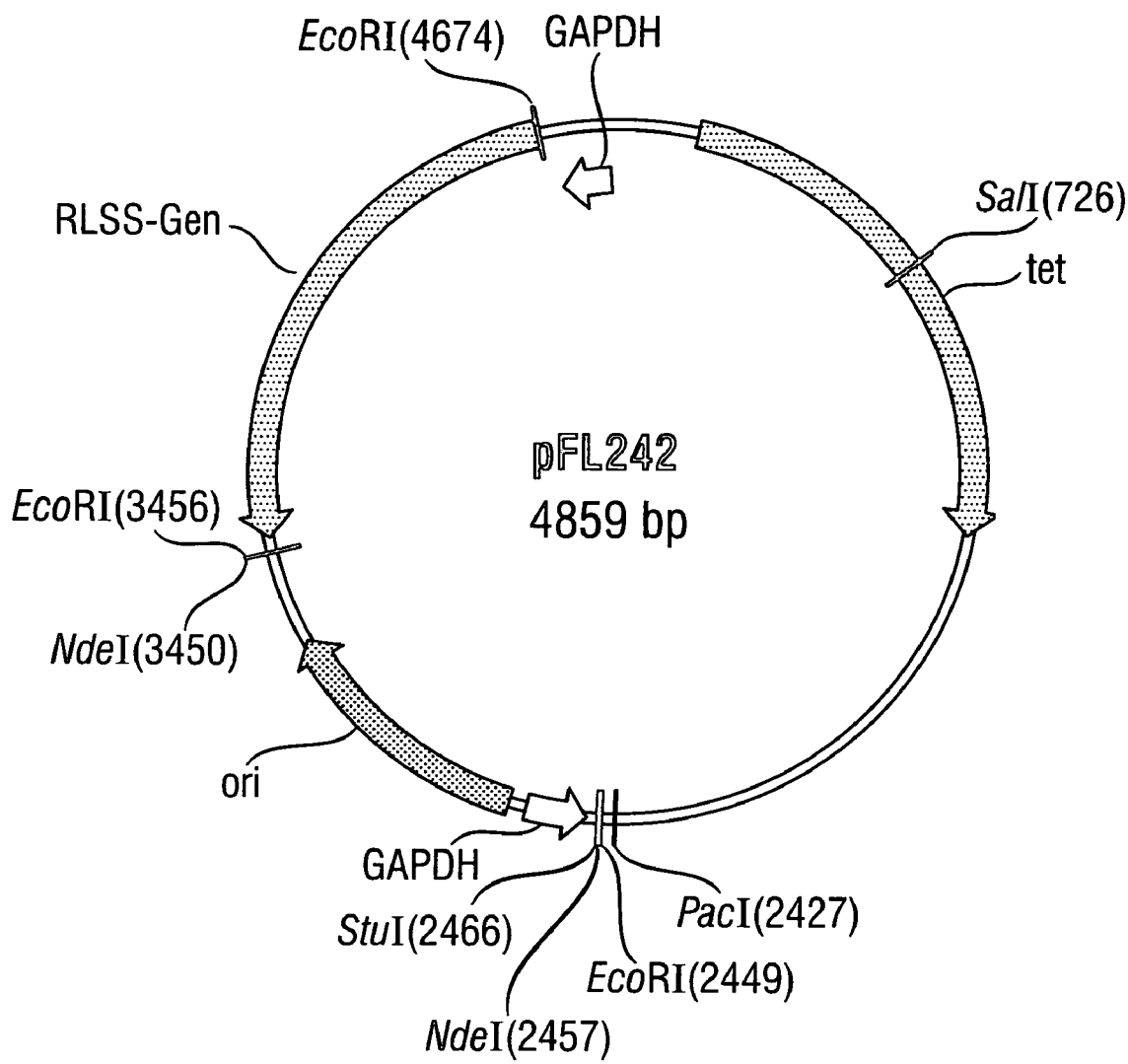

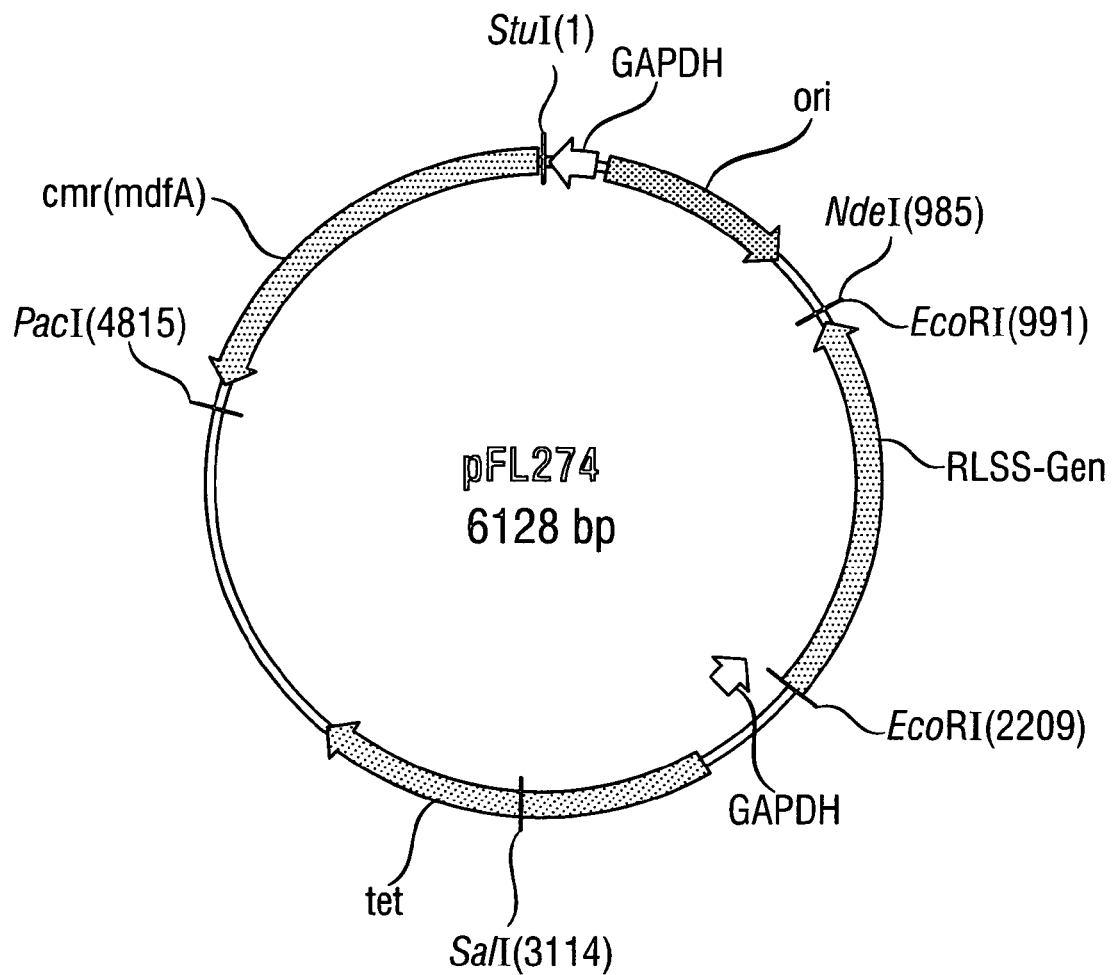
Fig. 2 pFL274

PROCESS FOR THE FERMENTATIVE PRODUCTION OF S-ADENOSYLMETHIONINE

CROSS-REFERENCE TO RELATED APPLICATIONS

This application claims the benefit of German Application No. 10 2005 009 751.0 filed Mar. 3, 2005. The entire disclosure of that application is hereby incorporated by reference.

BACKGROUND OF THE INVENTION

1. Field of the Invention

The invention relates to a process for the fermentative production of S-adenosylmethionine.

2. Background Art

S-Adenosylmethionine ("SAM") is an important methyl group donor in human metabolism and is used in the pharmaceutical field for the treatment of depression, diseases of the liver, and arthritis. A prior art process for SAM production comprises cultivation of yeasts (Schlenk and DePalma, J. Biol. Chem. 229, 1037-1050 (1957), Schlenk et al., Enzymologia 29, 283-298 (1965), Shiozaki et al., J. Biotechnol. 4, 345-354 (1986), Shiozaki et al., Agric. Biol. Chem. 53, 3269-3274 (1989)) in the presence of the precursor methionine and chromatographic purification of the SAM produced, after extraction from the cell lysate (U.S. Pat No. 4,562,149). SAM production by yeast is characterized by SAM being produced and stored intracellularly. In order to further process SAM, the cells must first be disrupted, as has been described, for example, in EP162323 (example 2) or in DE3329218 (example 1). Examples include chemical disruption methods, mechanical methods using a French press or high pressure homogenizers, and thermal processes (described in EP1091001, example 1).

In addition to SAM production by yeasts, the prior art also describes a bacterial SAM production process using *Eherichia coli* (*E. coli*), in which the bacteria excrete the SAM into the culture medium (EP 1 457 569 A1). Compared to the existing yeast processes, this fermentative SAM production process has a distinct advantage in that SAM is selectively secreted into the culture supernatant thereby simplifying the purification process. Since the culture supernatant contains only a few substances, secretion of SAM, therefore, already constitutes a first purification step facilitating further workup. This process for extracellular SAM production utilizes a SAM synthetase.

SUMMARY OF THE INVENTION

The present invention solves one or more problems of the prior art by providing in one embodiment a microorganism strain with increased production of SAM as compared to the prior art.

In another embodiment of the present invention, a method for producing SAM using the microorganism strain of the invention is provided. The method of this embodiment comprises fermenting a microorganism strain in a fermentation medium with SAM being secreted into said fermentation medium. The microorganism strain used in this method is the strain set forth above.

In another embodiment of the present invention, a method for preparing the microorganism strain set forth above is provided. The method of this embodiment comprises introducing a plasmid into a starting strain, the plasmid including a SAM synthetase gene and a cmr (mdfA) gene with a promoter.

BRIEF DESCRIPTION OF THE DRAWINGS

FIG. 1 is a schematic illustration of plasmid pFL242 the construction is described in Example 1;

FIG. 2 is a schematic illustration of plasmid pFL274 the construction is described in Example 2.

DETAILED DESCRIPTION OF THE PREFERRED EMBODIMENT(S)

Reference will now be made in detail to presently preferred compositions or embodiments and methods of the invention, which constitute the best modes of practicing the invention presently known to the inventors.

In an embodiment of the present invention, a microorganism strain secreting S-adenosylmethionine with an increased activity of the cmr (mdfA) gene product is provided. The microorganism strain of this embodiment has an increased activity of the cmr (mdfA) gene product as compared to the microorganisms of the prior art and as compared to a wild-type microorganism strain containing the cmr (mdfA) gene product. Moreover, the microorganism strain of the invention has an increased activity of the cmr (mdfA) gene product compared to the starting strain from which they are prepared.

In a variation of the present embodiment, a cell of said strain has an at least 2 fold increased activity of the cmr (mdfA) gene product as compared to a cell of a wild-type microorganism strain containing the cmr (mdfA) gene product. In another variation of the present embodiment, a cell of said strain has at least 5 fold increased activity of the cmr (mdfA) gene product as compared to a cell of a wild-type microorganism strain containing the cmr (mdfA) gene product. Experiments for determining the activity of the cmr (mdfA) gene product are described in scientific literature (see for example, Edgar and Bibi, J. Bacteriol. 179, 2274-2280). The *E. coli* cmr (mdfA) gene was identified as chloramphenicol export protein, Cmr, in 1996 (Nilsen et al., J. Bacteriol. 178, 3188-3193). The cmr (mdfA) gene was again described in 1997 as a multidrug efflux protein, MdfA, having a broad spectrum of substrates (Edgar and Bibi, J. Bacteriol. 179, 2274-2280). The entire disclosures of each scientific paper or patent cited in the disclosure of the present invention is hereby incorporated by reference. The Cmr (MdfA) protein belongs to the family of MF(S)[Major Facilliator (Superfamily)] transporters and transports both lipophilic, uncharged substrates such as, for example, chloramphenicol or erythromycin and lipophilic, positively charged substrates such as, for example, ethidium bromide, doxorubicin or benzalkonium in exchange for $H^+$ ions out of the cell (see review by Bibi et al., J. Mol. Microbiol. Biotechnol. 3, 171-177 (2001). Although the Cmr (MdfA) protein has a broad spectrum of substrates, it is surprising to the skilled worker that Cmr (MdfA) can act as an SAM export protein, since SAM has no structural similarities to the substrates described to date in the prior art. Furthermore, both the nucleic acid sequence of cmr (mdfA) and the amino acid sequence of the Cmr (MdfA) protein do not display any homologies to the previously known SAM transport genes and SAM transport proteins from yeast and humans. It is also not possible to predict, whether a substance can act as substrate for the Cmr (MdfA) protein, due to the largely unknown transport mechanism. Furthermore, it comes as a total surprise to the skilled worker that the cell of the microorganism strain of the invention exports with SAM a strongly hydrophilic, positively charged and, at the same time, important endogenous molecule.

In yet another embodiment of the present invention, a method of using the cmr (mdfA) gene product as an export protein in the production of SAM is provided. The cmr (mdfA) gene and the cmr (mdfA) gene product (Cmr (MdfA) protein) are characterized by the sequences SEQ ID NO. 1 and SEQ ID NO: 2, respectively. Within the scope of the present invention, cmr (mdfA) genes are also intended to include those genes which encode a protein having chloramphenicol-export or multidrug-efflux activity and which have a sequence identity to SEQ ID NO: 1 of greater than 30%, using the BESTFIT algorithm (GCG Wisconsin Package, Genetics Computer Group (GCG) Madison, Wis.). In a variation of the present invention, cmr (mdfA) genes include those genes which have a sequence identity to SEQ ID NO: 1 of greater than 50%. In a yet another variation of the present invention, cmr (mdfA) genes include those genes which have a sequence identity to SEQ ID NO: 1 of greater than 70%.

The Cmr (MdfA) proteins of the invention also include proteins having chloramphenicol-export or multidrug-efflux activity and a sequence identity to SEQ ID NO: 2 of greater than 15%, BESTFIT algorithm (GCG Wisconsin Package, Genetics Computer Group (GCG) Madison, Wis.). In a variation of the invention, the proteins have a sequence identity to SEQ ID NO: 2 of greater than 30%. In still another variation of the invention, the proteins have a sequence identity to SEQ ID NO: 2 of greater than 60%.

It should also be appreciated that the cmr (mdfA) genes of the invention also include allele variants of the cmr (mdfA) gene. In particular, the cmr (mdfA) genes of the invention include functional variants which derive from the sequence depicted in SEQ ID NO: 1 by deletion, insertion or substitution of nucleotides, with the enzymatic activity of the particular gene product being retained.

Microorganisms of the invention are generated using standard molecular-biological techniques known to those skilled in the art. Suitable starting strains include any microorganisms which exhibit the biosynthetic pathway for SAM, are accessible to recombinant processes, and culturable by way of fermentation. Examples of suitable microorganisms include, for example, fungi, yeasts or bacteria. In one variation of the present embodiment, suitable stains include bacteria of the phylogenetic group of Eubacteria. In another variation of this embodiment, suitable strains include microorganisms of the Enterobacteriaceae family such as the species Escherichia coli.

The increase in activity of the cmr (mdfA) gene product in the microorganism of the invention is achieved, for example, by increased expression of the cmr (mdfA) gene. In this connection, the copy number of the cmr (mdfA) gene in a microorganism may be elevated and/or expression of the cmr (mdfA) gene may be increased by means of suitable promoters. In one variation, increased expression means that the cmr (mdfA) gene is expressed at least twice as highly as in the starting strain. In another variation of the present embodiment, an increased copy number of the cmr (mdfA) gene means that at least one additional chromosomal and/or plasmid-encoded copy of the cmr (mdfA) gene is used compared to the starting strain.

The skilled worker can employ known methods in order to increase the copy number of the cmr (mdfA) gene in a microorganism. Thus it is possible, for example, to clone the cmr (mdfA) gene into plasmid vectors with multiple copies per cell (e.g. pUC19, pBR322, pACYC184 for *E. coli*) which are subsequently introduced into a microorganism. Alternatively, multiple copies of the cmr (mdfA) gene can be integrated into the chromosome of a microorganism. Integration processes which may be utilized include the known systems with temperate bacteriophages, integrative plasmids or integration via homologous recombination.

In a variation of the present invention, the copy number is increased by cloning a cmr (mdfA) gene into plasmid vectors under the control of a promoter. In a refinement of this variation, the copy number in *E. coli* is increased by cloning a cmr (mdfA) gene in a pACYC derivative.

The control region used for expression of a plasmid-encoded cmr (mdfA) gene may be the natural promoter and operator regions of said gene. Alternatively, expression of a cmr (mdfA) gene may also be increased by means of other promoters. Appropriate promoter systems such as, for example, the constitutive GAPDH promoter of the gapA gene or the inducible lac, tac, trc, lambda, ara or tet promoters in *E. coli* are known to those skilled in the art. Such constructs may be used in a manner known per se on plasmids or chromosomally.

Increased expression may furthermore be achieved by the presence of translation start signals such as, for example, the ribosome binding site or the start codon of the gene in an optimized sequence on the particular construct or by replacing rare codons, according to the codon usage, with more frequently occurring codons.

In another embodiment of the present invention, microorganism strains containing the modifications set forth above are provided.

A cmr (mdfA) gene is cloned into plasmid vectors, for example, by specific amplification by means of the polymerase chain reaction using specific primers which cover the complete cmr (mdfA) gene, and subsequent ligation with vector DNA fragments. Preferred vectors used for cloning a cmr (mdfA) gene are plasmids which already contain promoters for increased expression, for example, the constitutive GAPDH promoter of the *E. coli* gap A gene.

In a variation of the invention, vectors which already contain a gene/allele whose use results in increased biosynthesis of SAM are used. An example of such a vector contains a rat liver SAM synthetase (RLSS) allele or the metK gene (described in EP 0 647 712 A1 and EP 1 457 569 A1) or combinations of multiple SAM synthetases. It is, of course, also possible to use plasmids which contain multiple copies of the same SAM synthetase gene. Vectors of this kind enable microorganism strains of the invention with high SAM overproduction to be prepared directly from any microorganism strain.

The invention thus also relates to a plasmid which comprises a SAM synthetase gene and a cmr (mdfA) gene under the control of a promoter. Such a plasmid may also comprise combinations of SAM synthetase genes of various organisms or multiple copies of one SAM synthetase gene. The cmr (mdfA)-containing plasmids are introduced into microorganisms by well known transformation methods (e.g. electroporation) and selected for plasmid-carrying clones by, for example, resistance to antibiotics.

The invention thus also relates to processes for preparing a microorganism strain of the invention, which comprise introducing a plasmid of the invention into a starting strain. Useful strains for transformation with a plasmid of the invention are those which already have alleles which may likewise have a beneficial effect on SAM production. Examples of such alleles include alleles effecting improved SAM production, such as the RLSS gene or the metK gene (as described, for example, in EP 1 457 569 A1) or genes effecting improved methionine uptake, such as, for example, the *E. coli* metNIQ operon (Merlin et al., J. Bacteriol. 184, 5513-5517 (2002); Gál et al., J. Bacteriol. 184, 4930-4932 (2002); Zhang et al., Arch. Microbiol. 180, 88-100 (2003)) or genes having a beneficial effect on improved endogenous methionine synthesis, such as, for example, an improved homoserine transsuccinylase gene (JP2000139471A, DE-A-10247437, DE-A-10249642).

In yet another embodiment of the present invention, a method for producing SAM with the aid of the microorganism stains set forth above is provided. Typically, such SAM production is carried out in a fermenter by processes known in the art. The method of this embodiment comprises fermenting a microorganism strain of the invention in a fermentation medium with SAM being secreted into said fermentation medium. The SAM produced is preferably then removed from the fermentation broth. The microorganism strain is cultivated in the fermenter as a continuous culture, as a batch culture or, as a fed batch culture.

In a variation of the present embodiment, the microorganism strain is cultivated by metering a carbon source continuously into the culture medium during fermentation. Suitable carbon sources include, for example, sugars, sugar alcohols or organic acids. More particular carbon sources include, glucose, lactose or glycerol as carbon sources. In a further refinement of this variation, the carbon source is metered into the culture medium in a form which ensures that the carbon source content in the fermenter is maintained in a range from 0.1-50 g/l during fermentation. In another refinement, the carbon source is metered into the culture medium in a form which ensures that the carbon source content in the fermenter is maintained in a range from 0.5-10 g/l during fermentation. In a variation of the invention, nitrogen sources are added to the culture medium. Suitable nitrogen sources, include for example, ammonia, ammonium salts, and protein hydrolysates. When using ammonia for adjusting the pH stat, the nitrogen source is metered into the culture medium at regular intervals during fermentation. Additional additives which may be added to the culture medium include salts of the elements phosphorus, chlorine, sodium, magnesium, nitrogen, potassium, calcium, and iron. Salts of the elements molybdenum, boron, cobalt, manganese, zinc and nickel are optionally present in trace amounts (i.e. in µM concentrations). The culture medium may also include organic acids (e.g. acetate, citrate), amino acids (e.g. isoleucine) and vitamins (e.g. $B_1$, $B_{12}$) to the medium. Complex nutrient sources which may be used are, for example, yeast extract, corn steep liquor, soybean meal or malt extract. It is moreover possible to add to the medium, as a specific precursor for SAM synthesis, L-methionine or D/L-methionine in a concentration of between 0.05 and 25 g/l. In a variation, L-methionine or D/L-methionine is added in a concentration of between 1 and 7 g/l.

In addition, in a particularly preferred process of the invention, L-methionine or D,L-methionine are metered into the medium continuously during cultivation. In a variation of the invention, L-methionine or D/L-methionine are continuously metered into the culture medium at a rate between 0.05 g and 10 g per hour. In another variation of the invention, L-methionine or D/L-methionine are continuously metered into the culture medium at a rate between 0.1 g and 2 g per hour.

The incubation temperature for mesophilic microorganisms is typically from about 15 to about 45° C. In a variation, incubation temperature for mesophilic microorganisms is from about 30 to about 37° C.

The fermentation process of the invention is preferably carried out under aerobic growth conditions. Oxygen is introduced into the fermenter by using compressed air or pure oxygen. During fermentation, the pH of the fermentation medium is typically in the range from about 5.0 to about 8.5. In a variation, the pH of the fermentation medium is about 7.0. The strain is preferably incubated under aerobic culturing conditions over a period of from about 16 to 150 hours at a growth temperature optimal for the particular strain. In a variation, the culturing time is between 20 and 48 hours.

SAM may be removed from the culture medium by processes known to those skilled in the art, such as centrifugation of the medium to remove the cells, crossflow filtration for removing proteins and subsequent chromatographic purification, concentration, formulation or complexing of the product. Moreover, SAM produced in the process of the invention is detected and quantified. Chromatography (e.g. HPLC) is an example of a process that is useful for this latter process.

The following examples serve to further illustrate the invention.

EXAMPLE 1

Construction of the Plasmid pFL242

To clone the GAPDH promoter-RLSS fragment, plasmid pKP504 was linearized with the aid of the restriction endonuclease SspI. (Roche, Mannheim, Germany) Preparation of the pKP504 plasmid is described in EP-A-1 457 569, example 4. The linearized plasmid was then dephosphorylated with the aid of an alkaline phosphatase (Roche, Mannheim, Germany). Finally, the linearized vector was purified prior to ligation, using a QIAquick Nucleotide Removal Kit (Qiagen, Hilden, Germany) according to the manufacturer's instructions.

The GAPDH promoter-RLSS fragment was isolated from the SAM production plasmid pMSRLSSk (EP 1 457 569 A1) with the aid of the restriction endonucleases Ecl136II (Fermentas, St. Leon-Rot, Germany) and StuI (Roche, Mannheim, Germany). After purification of said fragment via agarose gel electrophoresis with subsequent gel extraction (QIAquick Gel Extraction Kit, Qiagen, Hilden, Germany), the GAPDH promoter-RLSS fragment and the SspI-linearized pKP504 vector were ligated by means of T4 DNA ligase (Roche, Mannheim, Germany) according to the manufacturer's instructions.

E. coli cells of the strain DH5α (Invitrogen, Karlsruhe, Germany) were transformed with the ligation mixture by means of electroporation in a manner known to the skilled worker. The transformation mixture was applied to LB-tetracycline agar plates (10 g/l tryptone, 5 g/l yeast extract, 5 g/l NaCl, 15 g/l agar, 20 mg/l tetracycline) and incubated at 37° C. overnight.

The desired transformants were identified by restriction analysis, after plasmid isolation by means of a QIAprep Spin Miniprep Kit (Qiagen, Hilden, Germany). It is then possible to clone another gene under the control of the constitutive GAPDH promoter of the E. coli gapA gene in the plasmid obtained in this way, pFL242 (FIG. 1). Plasmid pFL242 which was used for performing the examples was deposited with the DSMZ (Deutsche Sammlung für Mikroorganismen und Zellkulturen GmbH, D-38142 Brunswick, Germany) according to the Budapest Treaty under number DSM 17142 on Feb. 17, 2005.

EXAMPLE 2

Construction of the Plasmid pFL274

A. Amplification of the cmr (mdfA) Gene

The E. coli cmr (mdfA) gene was amplified by means of the polymerase chain reaction (PCR) using Taq DNA polymerase, according to common practice known to the skilled worker. Chromosomal DNA of the E. coli wild-type strain W3110 (ATCC 27325) was used as the template. The primers used were the oligonucleotides cmr for (SEQ ID NO: 3) with the sequence:

```
5'-AAA AGG CCT TGC ATG CAA AAT AAA TTA GCT TC-3'
        StuI
``` and cmr rev (SEQ ID NO: 4) with the sequence

```
5'-CCC TTA ATT AAA CCA GAT TGA CGA CCA TCA C-3'.
        PacI
```

The approx. 1.3 kb DNA fragment obtained in the PCR was then purified by means of a small DNA adsorption column from the QIAprep Spin Miniprep Kit (Qiagen, Hilden, Germany) according to the manufacturer's instructions.

B. Cloning of the cmr (mdfA) Gene into the pFL242 Vector

Two cleavage sites for restriction endonucleases StuI and PacI were introduced into the PCR fragment via primers cmr for and cmr rev. The purified PCR fragment was cut by the restriction endonucleases StuI (Roche, Mannheim, Germany) and PacI (New England Biolabs, Frankfurt am Main, Germany) under the conditions indicated by the manufacturer, fractionated on an agarose gel and then isolated from said agarose gel by means of the QIAquick Gel Extraction Kit (Qiagen, Hilden, Germany) according to the manufacturer's instructions.

To clone the cmr (mdfA) gene, the pFL242 vector was cut by the restriction enzymes StuI and PacI under the conditions indicated by the manufacturer. The plasmid was then dephosphorylated at the 5' ends by treatment with alkaline phosphatase (Roche, Mannheim, Germany) and then purified like the PCR fragment by means of the QIAquick Gel Extraction Kit (Qiagen, Hilden, Germany). The PCR fragment was ligated with the cut and dephosphorylated vector according to the manufacturer's instructions using T4 DNA ligase (Roche, Mannheim, Germany). E. coli cells of the strain W3110 (ATCC 27325) were transformed with the ligation mixture by means of electroporation in a manner known to the skilled worker. The transformation mixture was applied to LB-tetracycline agar plates (10 g/l tryptone, 5 g/l yeast extract, 5 g/l NaCl, 15 g/l agar, 20 mg/l tetracycline) and incubated at 37° C. overnight.

The desired transformants were identified by restriction analysis, after plasmid isolation by means of a QIAprep Spin Miniprep Kit (Qiagen, Hilden, Germany), and the correctness of the result was confirmed by sequence analysis.

In the plasmid obtained in this way, pFL274 (FIG. 2), the cmr (mdfA) gene is under the control of the GAPDH promoter.

EXAMPLE 3

Preparation of an S-adenosylmethionine Producer

The pFL274 plasmid described in example 2 was used for transforming the E. coli strain W3110 (ATCC 27325) by means of the $CaCl_2$ method and, after selection on LB agar plates containing 20 mg/l tetracycline, the plasmid was reisolated from one of the transformants, cleaved by restriction endonucleases and checked. Said strain is referred to as W3110/pFL274 and is suitable for production of SAM.

EXAMPLE 4

Fermentative Production of S-adenosylmethionine

A. Production of SAM

The strain W3110/pFL274 was used for fermentative production of SAM. Strains used for comparison were, firstly, the W3110 (ATCC 27325) wild-type strain without plasmid and, secondly, the W3110/pMSRLSSk strain, both of which were cultured under the same conditions. W3110/pMSRLSSk was prepared from W3110 and the plasmid pMSRLSSk, analogously to example 3.

The following medium was used for cultivation: for 1 l of medium: $CaCl_2 \times 2\ H_2O$ 0.0147 g, $MgSO_4 \times 7\ H_2O$ 0.3 g, $Na_2MoO_4 \times 2H_2O$ 0.15 mg, $H_3BO_3$ 2.5 mg, $CoCl_2 \times 6\ H_2O$ 0.7 mg, $CuSO_4 \times 5\ H_2O$ 0.25 mg, $MnCl_2 \times 4\ H_2O$ 1.6 mg, $ZnSO_4 \times 7\ H_2O$ 0.3 mg, $KH_2PO_4$ 3.0 g, $K_2HPO_4$ 12.0 g, $(NH_4)_2SO_4$ 5 g, NaCl 0.6 g, $FeSO_4 \times 7\ H_2O$ 0.002 g, $Na_3$ citrate $\times 2\ H_2O$ 1 g, glucose 15 g, tryptone 1 g, yeast extract 0.5 g.

For cultivation of W3110/pMSRLSSk and W3110/pFL274, 20 μg/ml tetracycline were added to the medium. Moreover, the medium contained a supplement of 0.5 g/l L-methionine.

First, as a preculture for production cultivation, 3 ml of medium were inoculated in a glass test tube with the particular strain and incubated on a shaker at 150 rpm and 37° C. for 16 h. Finally, 20 ml of the same medium were inoculated in a 100 ml Erlenmeyer flask with the cells prepared in this way to an $OD_{600}$ (absorption at 600 nm) of 0.1. The production cultures were incubated at 37° C. and 150 rpm on a shaker for up to 48 h. Samples were taken after 24 h and 48 h, and the cells were removed from the culture medium by centrifugation.

B. Quantification of the SAM Produced

The SAM present in the culture supernatant was quantified by means of HPLC, using a DEVELOSIL RP-Aqueous C 30 column, 5 μm, 250*4.6 mm (Phenomenex, Aschaffenburg, Germany) and 10 μL of culture supernatant applied were fractionated by means of isocratic elution with an eluent of 3 ml of 85% strength $H_3PO_4$ to 1lof $H_2O$ at a flow rate of 0.5ml/min and room temperature and quantified by means of a diode array detector at a wavelength of 260 nm. Table 1 depicts the SAM contents obtained in the particular culture supernatant.

TABLE 1

| Strain | S-Adenosylmethionine [mg/l] | |
|---|---|---|
| | 24 h | 48 h |
| W3110 | 0 | 0 |
| W3110/pMSRLSSk | 79 | 63 |
| W3110/pFL274 | 287 | 222 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An isolated *E. coli* cell which secrets S-adenosylmethionine as a result of a modification in said cell to increase the activity of the poypeptide of SEQ ID NO: 2 compared to the activity of the polypeptide of SEQ ID NO: 2 in the corresponding *E. coli* cell prior to modification, wherein said increase in ativity is due to over-expression of a nucleic acid encoding the polypeptide of SEQ ID NO: 2 by placing said nucleic acid under the control of a strong heterologous promoter.

2. The isolated *E. coli* cell of claim 1 wherein said *E. coli* cell exhibits at least 2 fold increased activity of the polypeptide of SEQ ID NO: 2 compared to the activity of the polypeptide SEQ ID NO: 2 in the corresponding *E. coli* cell prior to modification.

3. The isolated *E. coli* cell of claim 1 wherein said *E. coli* cell exhibits at least 5 fold increased activity of the polypeptide of SEQ ID NO: 2 compared to the activity of the polypeptide of SEQ ID NO: 2 in the corresponding *E. coli* cell prior to modification.

4. An isolated *E. coli* cell which secrets 5-adenosylmethionine as a result of a modification in said cell to increase the activity of the polypeptide of SEQ ID NO: 2 compared to the activity of the polypeptide of SEQ ID NO: 2 in the corresponding *E. coli* cell prior to modification, wherein said increase in activity is due to an increase in the copy number of a nucleic acid encoding the polypeptide of SEQ ID NO: 2.

5. The isolated *E. coli* cell of claim 4 wherein said *E. coli* cell exhibits at least 5 fold increased activity of the polypeptide of SEQ ID NO: 2 compared to the activity of the polypeptide of SEQ ID NO: 2 in the corresponding *E. coli* cell prior to modification.

6. The isolated *E. coli* cell of claim 4 wherein *E. coli* cell exhibits at least 5 fold increased activity of the polypeptide of SEQ ID NO: 2 compared to the activity of the polypeptide of SEQ ID NO: 2 in the corresponding *E.coli* cell prior to modification.

* * * * *

SEQUENCE LISTING

```
<160> NUMBER OF SEQ ID NOS: 4

<210> SEQ ID NO 1
<211> LENGTH: 1233
<212> TYPE: DNA
<213> ORGANISM: Escherichia coli
<220> FEATURE:
<221> NAME/KEY: geneS-adenosylmethionine
<222> LOCATION: (1)..(1230)
<300> PUBLICATION INFORMATION:
<301> AUTHORS: Edgar, Rotem
<302> TITLE: MdfA, an Escherichia coli multidrug resistance protein
      with an extraordinarily broad spectrum of drug
      recognition
<303> JOURNAL: J. Bacteriol.
<304> VOLUME: 179
<305> ISSUE: 7
<306> PAGES: 2274-2280

<400> SEQUENCE: 1
atgcaaaata aattagcttc cggtgccagg cttggacgtc aggcgttact tttccctctc       60
tgtctggtgc tttacgaatt ttcaacctat atcggcaacg atatgattca acccggtatg      120
ttggccgtgg tggaacaata tcaggcgggc attgattggg ttcctacttc gatgaccgcg      180
tatctggcgg gcgggatgtt tttacaatgg ctgctggggc cgctgtcgga tcgtattggt      240
cgccgtccgg tgatgctggc gggagtggtg tggtttatcg tcacctgtct ggcaatattg      300
ctggcgcaaa acattgaaca attcaccctg ttgcgcttct tgcagggcat aagcctctgt      360
ttcattggcg ctgtgggata cgccgcaatt caggaatcct tcgaagaggc ggtttgtatc      420
aagatcaccg cgctgatggc gaacgtggcg ctgattgctc cgctacttgg tccgctggtg      480
ggcgcggcgt ggatccatgt gctgccctgg gaggggatgt ttgttttgtt tgccgcattg      540
gcagcgatct ccttttttcgg tctgcaacga gccatgcctg aaaccgccac gcgtataggc      600
gagaaactgt cactgaaaga actcggtcgt gactataagc tggtgctgaa gaacggccgc      660
tttgtggcgg gggcgctggc gctgggattc gttagtctgc cgttgctggc gtggatcgcc      720
cagtcgccga ttatcatcat taccggcgag cagttgagca gctatgaata tggcttgctg      780
caagtgccta ttttcggggc gttaattgcg ggtaacttgc tgttagcgcg tctgacctcg      840
cgccgcaccg tacgttcgct gattattatg ggcggctggc cgattatgat tggtctattg      900
gtcgctgctc cggcaacggt tatctcatcg cacgcgtatt tatggatgac tgccgggtta      960
agtatttatg ctttcggtat tggtctggcg aatgcgggac tggtgcgatt aaccctgttt     1020
```

```
gccagcgata tgagtaaagg tacggtttct gccgcgatgg gaatgctgca aatgctgatc   1080
tttaccgttg gtattgaaat cagcaaacat gcctggctga acgggggcaa cggactgttt   1140
aatctcttca accttgtcaa cggaattttg tggctgtcgc tgatggttat cttttaaaa    1200 gataaacaga tgggaaattc tcacgaaggg taa                                1233
```

<210> SEQ ID NO 2
<211> LENGTH: 410
<212> TYPE: PRT
<213> ORGANISM: Escherichia coli
<300> PUBLICATION INFORMATION:
<301> AUTHORS: Edgar, Rotem
<302> TITLE: MdfA, an Escherichia coli multidrug resistance protein
      with an extraordinarily broad spectrum of drug
      recognition
<303> JOURNAL: J. Bacteriol.
<304> VOLUME: 179
<305> ISSUE: 7
<306> PAGES: 2274-2280
<313> RELEVANT RESIDUES: 1 TO 410

<400> SEQUENCE: 2

```
Met Gln Asn Lys Leu Ala Ser Gly Ala Arg Leu Gly Arg Gln Ala Leu
 1               5                  10                  15

Leu Phe Pro Leu Cys Leu Val Leu Tyr Glu Phe Ser Thr Tyr Ile Gly
             20                  25                  30

Asn Asp Met Ile Gln Pro Gly Met Leu Ala Val Val Glu Gln Tyr Gln
         35                  40                  45

Ala Gly Ile Asp Trp Val Pro Thr Ser Met Thr Ala Tyr Leu Ala Gly
     50                  55                  60

Gly Met Phe Leu Gln Trp Leu Leu Gly Pro Leu Ser Asp Arg Ile Gly
 65                  70                  75                  80

Arg Arg Pro Val Met Leu Ala Gly Val Val Trp Phe Ile Val Thr Cys
                 85                  90                  95

Leu Ala Ile Leu Leu Ala Gln Asn Ile Glu Gln Phe Thr Leu Leu Arg
            100                 105                 110

Phe Leu Gln Gly Ile Ser Leu Cys Phe Ile Gly Ala Val Gly Tyr Ala
        115                 120                 125

Ala Ile Gln Glu Ser Phe Glu Glu Ala Val Cys Ile Lys Ile Thr Ala
    130                 135                 140

Leu Met Ala Asn Val Ala Leu Ile Ala Pro Leu Leu Gly Pro Leu Val
145                 150                 155                 160

Gly Ala Ala Trp Ile His Val Leu Pro Trp Glu Gly Met Phe Val Leu
                165                 170                 175

Phe Ala Ala Leu Ala Ala Ile Ser Phe Phe Gly Leu Gln Arg Ala Met
            180                 185                 190

Pro Glu Thr Ala Thr Arg Ile Gly Glu Lys Leu Ser Leu Lys Glu Leu
        195                 200                 205

Gly Arg Asp Tyr Lys Leu Val Leu Lys Asn Gly Arg Phe Val Ala Gly
    210                 215                 220

Ala Leu Ala Leu Gly Phe Val Ser Leu Pro Leu Leu Ala Trp Ile Ala
225                 230                 235                 240

Gln Ser Pro Ile Ile Ile Ile Thr Gly Glu Gln Leu Ser Ser Tyr Glu
                245                 250                 255

Tyr Gly Leu Leu Gln Val Pro Ile Phe Gly Ala Leu Ile Ala Gly Asn
            260                 265                 270

Leu Leu Leu Ala Arg Leu Thr Ser Arg Arg Thr Val Arg Ser Leu Ile
```

-continued

```
            275                 280                 285
Ile Met Gly Gly Trp Pro Ile Met Ile Gly Leu Leu Val Ala Ala Ala
    290                 295                 300

Ala Thr Val Ile Ser Ser His Ala Tyr Leu Trp Met Thr Ala Gly Leu
305                 310                 315                 320

Ser Ile Tyr Ala Phe Gly Ile Gly Leu Ala Asn Ala Gly Leu Val Arg
                325                 330                 335

Leu Thr Leu Phe Ala Ser Asp Met Ser Lys Gly Thr Val Ser Ala Ala
                340                 345                 350

Met Gly Met Leu Gln Met Leu Ile Phe Thr Val Gly Ile Glu Ile Ser
                355                 360                 365

Lys His Ala Trp Leu Asn Gly Gly Asn Gly Leu Phe Asn Leu Phe Asn
        370                 375                 380

Leu Val Asn Gly Ile Leu Trp Leu Ser Leu Met Val Ile Phe Leu Lys
385                 390                 395                 400

Asp Lys Gln Met Gly Asn Ser His Glu Gly
                405                 410

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide cmr for

<400> SEQUENCE: 3
aaaaggcctt gcatgcaaaa taaattagct tc                               32

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide cmr rev

<400> SEQUENCE: 4
cccttaatta aaccagattg acgaccatca c                                31
```